US00PP13148P2

(12) United States Plant Patent
Heims

(10) Patent No.: US PP13,148 P2
(45) Date of Patent: Oct. 29, 2002

(54) TIARELLA PLANT NAMED 'STARFISH'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/901,931

(22) Filed: Jul. 9, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Klarquist Sparkman, LLP

(57) ABSTRACT

A new and distinct hybrid of Tiarella characterized by its dwarf habit and unique lobed leaves of marked coloration.

1 Drawing Sheet

BOTANICAL CLASSIFICATION

*Tiarella hybrid* cvs Starfish.

The present invention relates to a new and distinct hybrid of Tiarella, of the family Saxifragaceae, which originated from a cross between unknown parents. This new Tiarella was one of many seedlings grown from select plants that were mass pollinated in the greenhouse in Canby, Oreg. Since both parents and the instant plant are interspecific hybrids from several generations of interbreeding and selecting, no species designations are given.

The new variety has been reproduced only by asexual propagation (division and micropropagation). Each of the progeny exhibits identical characteristics to the original plant.

This plant is characterized by the following:

1. Dwarf habit.
2. Unique lobed foliage shape with dark coloration on the veins.
3. Non-stoloniferous habit.
4. Good reblooming.

Asexual propagation as done by division and micropropagation, in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The FIGURE is a picture of Tiarella 'Starfish' in bloom in the garden in June in Canby, Oreg.

DETAILED PLANT DESCRIPTION

The following is a detailed description of the new Tiarella hybrid based on observations of two-year-old plants grown in one-gallon pots in Canby, Oreg. The color descriptions are all based on The Royal Horticultural Society Colour Chart.

Plant:
- *Type.*—Herbaceous perennial.
- *Hardiness.*—USDA Zones 5 to 9.
- *Form.*—Basal clump.
- *Size.*—30 cm. wide and 13 cm. high.

Foliage:
- *Type.*—Simple.
- *Arrangement.*—Rosette.
- *Shape.*—Ovate. Variable.
- *Lobing.*—Palmately 5-parted, with each of the five main lobes lobed again, the terminal up to 4 times and the lateral main lobes one to three times. Separation between the lobes is substantial giving the "starfish" appearance.
- *Margins.*—Entire to slightly crenate with scabrous hairs.
- *Venation.*—Palmate.
- *Apex.*—Apiculate.
- *Base.*—Cordate, overlapping.
- *Length.*—Variable, 5 to 7.5 cm.
- *Width.*—Variable, 4.5 to 7.5 cm.
- *Petiole length.*—7 to 11.5 cm.
- *Petiole color.*—Greyed purple 187A.
- *Texture.*—Rough, scabrous.
- *Aspect.*—Matte.
- *Surface.*—Hispid, on the top and bottom surfaces with bottom hairs shorter, giving the leaf a rough texture.
- *Leaf color.*—Topside — Green 137A with the five main veins dotted with maroon, Greyed Purple 187B. Bottomside — Closest to 146C.

Inflorescence:
- *Type.*—Raceme.
- *Flower number.*—60 blooms per raceme.
- *Bloom period.*—April to May with sporadic rebloom throughout the summer and fall.
- *Peduncle.*—Height — 22 cm. Width — 1.5 mm. at the widest point. Color — Greyed Purple 187A to B becoming grayer half way up (closest to Grey 201A). Texture — Puberulent.
- *Pedicel.*—Length — 0.7 cm. Texture — Puberulent. Color — Greyed Purple 186C when flowering, becomes grayer with seed set.

Flower bud:
- *Size.*—0.2 cm.
- *Description.*—Puberulent, downfacing, campanulate when opening.
- *Color.*—Light pink, Red 56A.

Flower:
- *Type.*—Perfect, actinomorphic, sepals petaloid.
- *Shape.*—Stellate, outfacing. Petals and sepals similar in color and size.

*Petal and sepal number.*—5 petals, 5 fused sepals.
*Flower size.*—1 cm. wide and 0.9 cm. deep including stamens.
*Petal shape.*—Lanceolate with a clawed base.
*Petal size.*—0.55 cm long and 0.1 cm. wide.
*Petal color.*—Light pink, RHS Red Group 56D.
*Calyx.*—Campanulate, parted almost to the base.
*Calyx size.*—0.35 cm. wide and 0.1 cm. deep.
*Calyx color.*—Light pink, RHS Red Group 56B to D.
*Stamens.*—10, filaments RHS 56D, 0.5 cm long.
*Pollen color.*—RHS Greyed-Orange Group 167B.
*Pistil.*—1, white (RHS 155D), 0.3 cm long.
*Fragrance.*—Slight spicy fragrance is noted.
*Fertility.*—Tiarella 'Starfish' is sterile and no seeds are produced.

Fruit:
*Type.*—A one-celled capsule, beak-like, composed of two unequal parts.
*Size.*—0.4 cm long.
*Color.*—Grey-Brown 199B.

Seeds: None observed.

Disease resistance: This new hybrid shows good mildew tolerance, the main problem for Tiarella.

Comparisons With Similar Tiarella

Compared with Tiarella 'Mint Chocolate' (U.S. Plant Pat. No. 11,379), Tiarella 'Starfish' has a much smaller habit and broader leaf lobes with each main lobed again.

Compared with Tiarella 'Black Velvet' (U.S. Plant patent application Ser. No. 09-280,772), Tiarella 'Starfish' has a much smaller habit and much less crenate margins.

I claim:

1. A new and distinct hybrid of Tiarella plant substantially as shown and described, characterized by its small habit and unique cut leaves of marked coloration.

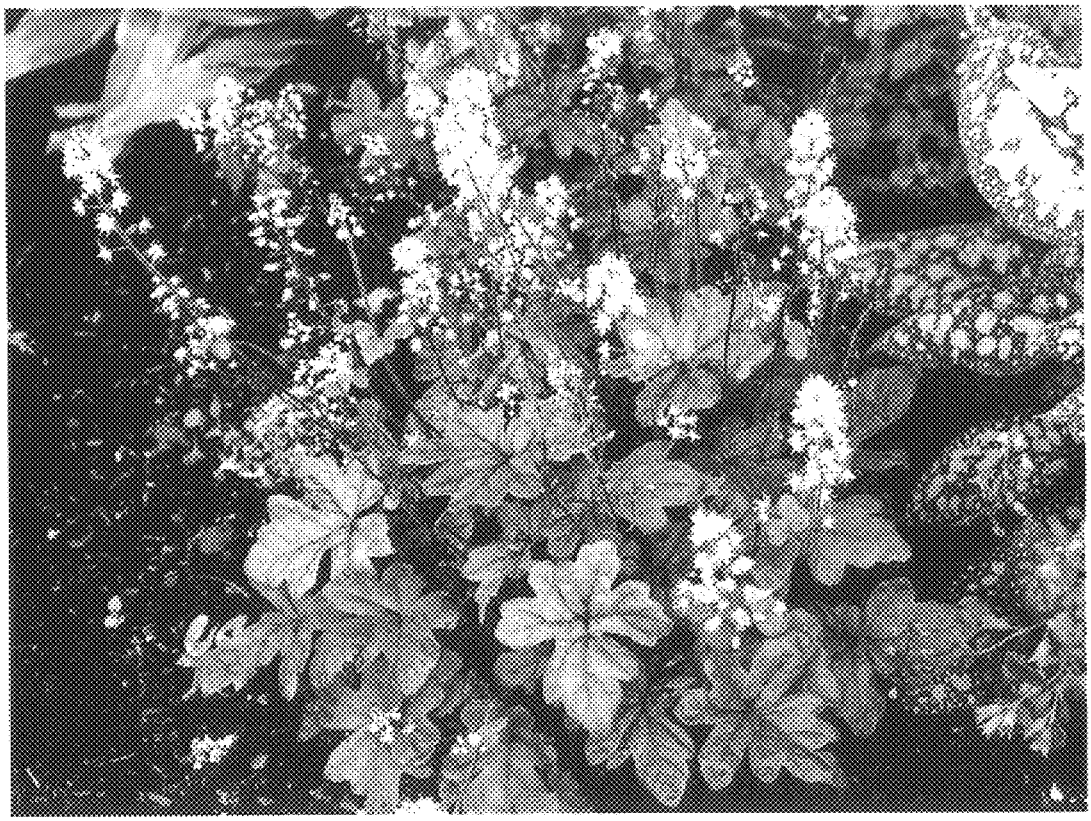

* * * * *